United States Patent [19]
Kemp et al.

[11] Patent Number: 5,453,267
[45] Date of Patent: Sep. 26, 1995

[54] SUNSCREEN COMPOSITIONS

[75] Inventors: Colyn R. Kemp; Judy A. Rolfe, both of Nottingham, United Kingdom

[73] Assignee: Boots Company PLC, United Kingdom

[21] Appl. No.: 173,146

[22] Filed: Dec. 23, 1993

Related U.S. Application Data

[63] Continuation of Ser. No. 752,516, Jul. 30, 1991, abandoned.

[30] Foreign Application Priority Data

Feb. 28, 1989 [GB] United Kingdom ............... 8904490

[51] Int. Cl.$^6$ ................ A61K 7/42; A61K 7/44; A61K 9/12
[52] U.S. Cl. ............... 424/59; 424/60; 514/844; 514/847; 514/938; 106/436
[58] Field of Search ................................ 424/59

[56] References Cited

U.S. PATENT DOCUMENTS

| | | | |
|---|---|---|---|
| 3,017,283 | 1/1962 | Bennetch et al. | 106/304 |
| 3,127,280 | 3/1964 | Whatley | 106/300 |
| 3,697,642 | 10/1972 | Madigan | 574/972 |
| 4,126,591 | 11/1978 | Kronstein et al. | 260/22 A |
| 4,328,040 | 5/1982 | Panek et al. | 106/300 |
| 4,857,308 | 8/1989 | Fukasawa et al. | 424/63 |

FOREIGN PATENT DOCUMENTS

| | | | |
|---|---|---|---|
| 2184356 | 4/1989 | United Kingdom | 424/59 |
| 2217987 | 11/1989 | United Kingdom | 424/59 |

OTHER PUBLICATIONS

Seifen–Ole–Fette–Wachse 113 (20), 10 Dec. 1987, Augsburg, W. Germany, pp. 765–771.
S. T. N., File Supplier, Karlsruhe, W. Germany, File C.A., vol. 19, No. 16, 16 Apr. 1979 (Columbus, Ohio).
Chemical Abstract 127377s.
K. Schrader, Grundlagen und Rezepturen der Kosmetika (Cosmetic Principles and Formulations) 1979, Dr. Alfred Hüthig Verlog, pp. 155–156(2).
U. Kaoru, K. Takashi, Proceedings of the 8th Intern. Congress of Rheology (1980, Plenum), vol. 3, pp. 615–620(2).

*Primary Examiner*—Dale R. Ore
*Attorney, Agent, or Firm*—Ostrolenk, Faber, Gerb & Soffen

[57] ABSTRACT

The invention relates to titanium dioxide sunscreen compositions containing 0.025 to 30% by weight of phosphate anions. Phosphate anions, preferably in the form of salts, have been found to prevent or reduce the rate of discolouration of titanium dioxide-containing sunscreen compositions caused by light catalysed reduction of titanium (IV) to titanium (III). Discolouration caused by the presence of parahydroxybenzoic acid esters or para-aminobenzoic acids, esters or derivatives thereof in such compositions has also been found to be reduced by the incorporation of phosphate salt.

Titanium dioxide particles having a mean primary particle size of less than 100 nm, each of the particles being substantially coated with phosphate anions are also described for use in sunscreen compositions.

12 Claims, No Drawings

SUNSCREEN COMPOSITIONS

This is a continuation of application Ser. No. 07/752,516 filed on Jul. 30, 1991, now abandoned.

The present invention relates to sunscreen compositions. The term "sunscreen" is used herein to encompass sun-screening compositions such as moisturisers, day creams, tanning lotions and sunblockers which are intended for topical application to provide protection against the sun's rays or other sources of ultraviolet (UV) radiation. The invention further relates to coated titanium dioxide particles for use in sunscreen compositions.

Conventional sunscreen compositions have been prepared either as oil-in-water or water-in-oil emulsions containing organic sunscreen agents which could be formulated equally successfully in either of the above emulsion systems. More recently sunscreen compositions have been proposed which contain titanium dioxide as the sunscreening agent.

The applicants have noted that sunscreen compositions containing titanium dioxide particles are prone to discolouration during storage. One type of discolouration arises during anaerobic storage and appears to be caused by light-catalysed reduction of the white titanium (IV) oxide to a less stable purple-blue coloured titanium (III) species. The discolouration occurs primarily as a surface effect, for example at the inside surfaces of containers filled with titanium dioxide sunscreen compositions. External light, in particular UV radiation, may be transmitted through the container material and may then catalyse reduction of titanium (IV) oxide at the surface of the composition within. Although the effect is restricted to the outer surfaces of such compositions and does not significantly reduce the sun-screening properties of the bulk composition, the surface discolouration, where visible, is aesthetically unacceptable to the consumer.

Another type of discolouration has been noted in titanium dioxide containing compositions which also incorporate parahydroxybenzoate esters, known for use as preservatives, or para-aminobenzoic acids, esters or derivatives thereof, known for use as sunscreening agents in their own right. These compounds appear to associate with the titanium dioxide particles and the resulting complexes produce an unacceptable yellowing of the sunscreen compositions.

We have now found that the discolouration of sunscreen compositions containing titanium dioxide can be substantially reduced or prevented by the incorporation of phosphate anions.

The present invention provides a sunscreen composition comprising:
  a) 0.5 to 30% by weight of titanium dioxide having a mean primary particle size of less than 100 nm; and
  b) 0.025 to 30% by weight of phosphate anions.

Phosphate anions may be provided in the form of inorganic phosphorus oxo acids, orthophosphates, pyrophosphates or condensed phosphates such as polyphosphates and metaphosphates. Preferably the phosphate anions are provided in the form of phosphate salts. Suitable phosphate salts include cosmetically acceptable alkali metal phosphates such as monosodium phosphate, disodium phosphate, trisodium phosphate, monopotassium phosphate, dipotassium phosphate and tripotassium phosphate, polyphosphates such as trisodium polyphosphate, pyrophosphates such as tetrasodium pyrophosphate, and mixtures thereof. Preferably a ratio of appropriate phosphate salts is used to give a buffer pH of between 4 and 8, more usually between pH 5 and 7. For example a ratio of monosodium phosphate:disodium phosphate of 4:1 gives a convenient buffer pH of about 6. However, where a single phosphate salt, a non-buffering mixture of phosphate salts or a phosphorus oxo acid is used as the source of phosphate anions, lower or higher pH's, for example between pH 2 and pH 12, may result without adversely affecting the advantageous properties of the compositions.

Discolouration of titanium dioxide compositions is proportional to the amount of titanium dioxide present and thus at higher levels of titanium dioxide correspondingly higher levels of phosphate anions are required. Generally the amount of phosphate anions employed will be 0.5 to 300%, preferably 3 to 200% by weight of the titanium dioxide incorporated into the compositions. More particularly, the phosphate anions are provided in the form of phosphate salts which comprise 5 to 150%, preferably 30 to 120%, by weight of the titanium dioxide in the compositions, for example, 100% by weight.

The amount of titanium dioxide present in any particular sunscreen composition according to the present invention depends on the use for which the composition is intended. Amounts of between 0.5 and 3% may be sufficient in the so-called suntanning products, day creams and moisturisers which are not intended to prevent the sun's rays reaching the skin. Usually the amount of phosphate salt in such compositions will be 0.15 to 4%, more usually 0.25 to 3.5%, preferably 0.25 to 3% of the composition. However, the so-called sunblock compositions which are intended to prevent substantially all of the sun's rays reaching the skin may require levels of titanium dioxide as high as 30%, for example 1 to 20%, preferably 2.5 to 10% of titanium dioxide. The amount of phosphate salt in such compositions will generally be in the range of 1 to 30%, more usually 1 to 20%, for example 1 to 10% of the composition.

The titanium dioxide preferably has a mean primary particle size of between 1 and 100 nm, more preferably between 5 and 50 nm, most preferably between 10 and 35 nm. Titanium dioxide of the above mean primary particle size is usually referred to as "microfine". The titanium dioxide may have an anatase, rutile or amorphous structure. The particles may be uncoated or may be provided with a coating of an aluminium compound such as aluminium oxide, aluminium stearate or aluminium laurate. Microfine titanium dioxide is available from Degussa under the trade designation P25 and from Teikoku Kako Co. Ltd. under the trade designation MT150W, MT600B or MT500B. Titanium dioxide coated with aluminium stearate is available from Teikoku Kako Co. Ltd. under the trade designation MT100T and titanium dioxide coated with aluminium oxide is available from Miyoshi under the trade designation UFTR. Generally, coated titanium dioxide discolours less rapidly than uncoated titanium dioxide but the addition of phosphate anions significantly improves the storage properties of compositions containing either coated or uncoated titanium dioxide.

The applicants have found that phosphate anions associate with titanium dioxide to form phosphate-coated titanium dioxide particles. The bonding of phosphate anions to titanium dioxide particles may arise spontaneously in situ within a sunscreen composition in which both titanium dioxide and phosphate anions are present or may occur during a preliminary coating procedure, prior to the introduction of titanium dioxide particles into a sunscreen composition. Accordingly, the present invention further provides titanium dioxide particles having a mean primary particle size of less than 100 nm, each of said particles being substantially coated with phosphate anions. It will be understood that the phrases "titanium dioxide particles substantially coated with phosphate anions" and "phosphate-coated titanium dioxide" as used herein describe particles of titanium dioxide to which a substantial number of phosphate anions are bonded. Phosphate-coated titanium dioxide particles have been found to be particularly advantageous for use in water-in-oil emulsions.

Preferably the phosphate anions are provided by a phosphate salt such as, for example, disodium phosphate or sodium polyphosphate. The ratio of phosphate salt to titanium dioxide used to prepare the particles according to the invention is generally, on a weight:weight basis, in the range 0.001 to 60:1, preferably 0.07 to 10:1. More particularly the phosphate salt used to prepare the particles according to the invention represents 3 to 200%, preferably 15 to 150%, more preferably 30 to 120% by weight of the titanium dioxide.

The particles of the present invention may be prepared by dispersing titanium dioxide into an aqueous solution of phosphate salt. The aqueous solution may be removed by filtration and the titanium dioxide particles washed, dried and milled to produce a fine, free-flowing powder of phosphate-coated titanium dioxide particles.

Parahydroxybenzoate esters (parabens) such as, for example, methyl, propyl and benzyl parabens are commonly used preservatives in the cosmetic industry and are used to control yeast and mould growths in particular. Mixtures of different parabens esters are particularly effective as preservatives and several proprietary blends of parabens esters are available. Unfortunately, when such parabens compounds come into contact with titanium dioxide a permanent yellow colouration often results. The applicants have found that this yellow colouration is reduced in the sunscreen compositions according to the present invention and accordingly a further aspect of our invention provides a sunscreen composition as hereinbefore described which further comprises 0.01 to 5% by weight, preferably 0.05 to 2%, of parabens ester. Where a mixture of parabens esters is used, each parabens ester preferably comprises 0.05 to 1% by weight of the sunscreen composition.

It has been shown that the liquid phase (oil or water) into which the parabens esters are first mixed during the formulation process and the stage of the formulation process at which they are added do not affect the advantageous properties of the resultant compositions.

Other sunscreening agents may be incorporated into the compositions of the present invention. Examples of suitable further sunscreening agents include:

a) para-aminobenzoic acids, esters and derivatives thereof, for example, 2-ethylhexyl para-dimethylaminobenzoate and the octyl ester of para-aminobenzoic acid;

b) methoxycinnamate esters such as 2-ethylhexyl para-methoxycinnamate, 2-ethoxyethyl para-methoxycinnamate or α,β-di-(para-methoxycinnamoyl)-α'-(2-ethylhexanoyl)-glycerin;

c) benzophenones such as oxybenzone;

d) dibenzoylmethanes; and e) salicylate esters.

Any additional sunscreening agent may be present in an amount of 0.1 to 10% by weight of the composition.

The applicants have also noted that the gradual yellowing which occurs in sunscreen compositions containing para-aminobenzoic acids or esters or derivatives thereof, particularly in oil-in-water compositions, is also reduced in the sunscreen compositions according to the invention and accordingly a still further aspect of the present invention provides a sunscreen composition comprising:

a) 0.5 to 30% by weight of titanium dioxide having a mean primary particle size of less than 100 nm;

b) 0.025 to 30% by weight of phosphate anions; and c) 0.1 to 10% by weight of a para-aminobenzoic acid, an ester thereof or a derivative thereof.

The use of phosphate anions to substantially prevent or reduce discolouration of sunscreen compositions containing titanium dioxide is novel and provides a further aspect of the invention.

The compositions or particles according to the present invention may be incorporated into sunscreen products such as oil phase dispersions or emulsions in the conventional way. Thus, a preferred embodiment of the present invention provides a sunscreen composition comprising an oil-in-water emulsion which comprises:

a) 0.5 to 30% by weight of titanium dioxide having a mean primary particle size of less than 100 nm;

b) 0.025 to 30% by weight of phosphate salt;

c) 5 to 40% by weight of an oil phase;

d) 1 to 20% by weight of an emulsifier; and e) preferably at least 40% by weight of an aqueous phase.

An alternative embodiment of the invention provides a sunscreen composition comprising a water-in-oil emulsion which comprises:

a) 0.5 to 30% by weight of titanium dioxide having a mean primary particle size of less than 100 nm;

b) 0.025 to 30% by weight of phosphate salt;

c) 5 to 50% by weight of an oil phase;

d) 1 to 15% by weight of an emulsifier; and e) preferably at least 40% by weight of an aqueous phase.

The oil phase of the oil phase dispersions and the water-in-oil and oil-in-water emulsions of the present invention may comprise for example:

a) hydrocarbon oils such as paraffin or mineral oils;

b) waxes such as beeswax or paraffin wax;

c) natural oils such as sunflower oil, apricot kernel oil, shea butter or jojoba oil;

d) silicone oils such as dimethicone, cyclomethicone or cetyldimethicone;

e) fatty acid esters such as isopropyl palmitate or isopropyl myristate;

f) fatty alcohols such as cetyl alcohol or stearyl alcohol; or g) mixtures thereof, for example, the blend of waxes available commercially under the trade name Cutina (Henkel).

In preferred water-in-oil compositions of the present invention the oil phase comprises 5 to 40%, more preferably 10 to 30% by weight of the composition. In preferred oil-in-water compositions of the present invention the oil phase comprises 5 to 30%, more preferably 10 to 20% by weight of the composition.

The emulsifiers used may be any emulsifiers known in the art for use in water-in-oil or oil-in-water emulsions. It has been found that particularly effective water-in-oil and oil-in-water sunscreen compositions can be prepared by using an emulsifier or mixture of emulsifiers selected from known cosmetically acceptable emulsifiers which include:

a) sesquioleates such as sorbitan sesquioleate, available commercially for example under the trade name Arlacel 83 (ICI), or polyglyceryl-2-sesquioleate;

b) ethoxylated esters of derivatives of natural oils such as the polyethoxylated ester of hydrogenated castor oil available commercially for example under the trade name Arlacel 989 (ICI);

c) silicone emulsifiers such as silicone polyols available commercially for example under the trade name ABIL WS08 (Th. Goldschmidt AG);

d) anionic emulsifiers such as fatty acid soaps e.g. potassium stearate and fatty acid sulphates e.g. sodium cetostearyl sulphate available commercially under the trade name Dehydag (Henkel);

e) ethoxylated fatty alcohols, for example the emulsifiers available commercially under the trade name Brij (ICI);

f) sorbitan esters, for example the emulsifiers available commercially under the trade name Span (ICI);

g) ethoxylated sorbitan esters, for example the emulsifiers available commercially under the trade name Tween (ICI);

h) ethoxylated fatty acid esters such as ethoxylated stearates, for example the emulsifiers available commercially under the trade name Myrj (ICI);

i) ethoxylated mono-, di-, and tri-glycerides, for example the emulsifiers available commercially under the trade name Labrafil (Alfa Chem.);

j) non-ionic self-emulsifying waxes, for example the wax available commercially under the trade name Polawax- (Croda);

k) ethoxylated fatty acids, for example, the emulsifiers available commercially under the trade name Tefose (Alfa Chem.); or l) mixtures thereof.

The amount of emulsifier present in the water-in-oil compositions of the present invention is preferably in the range 2 to 10%. Preferred water-in-oil emulsifiers are anionic or non-ionic emulsifiers. The amount of emulsifier present in the oil-in-water compositions of the present invention is preferably in the range 1 to 15%, more preferably 2 to 15%. Preferred oil-in-water emulsifiers include ethoxylated fatty acids and alcohols, ethoxylated stearates and ethoxylated triglycerides and mixtures thereof.

The compositions of the present invention may additionally comprise other components which will be well known to those skilled in the art. These include, for example, emolients such as isopropyl myristate or triglycerides of fatty acids e.g. lauric triglyceride or capric/caprylic triglyceride, such as the triglyceride available commercially under the trade name Migliol 810 (Huls UK); moisturisers such as D-panthenol; humectants such as glycerin or 1,3-butylene glycol; antioxidants such as DL-α-tocopherylacetate or butylated hydroxytoluene; emulsion stabilising salts such as sodium chloride, sodium citrate or magnesium sulphate; film formers to assist spreading on the surface of the skin such as alkylated polyvinylpyrrolidone e.g. available commercially under the trade name Antaron (GAF); thickeners such as acrylic acid polymers e.g. available commercially under the trade name Carbopol (B. F. Goodrich) or modified celluloses e.g. hydroxyethylcellulose available commercially under the trade name Natrosol (Hercules); preservatives such as bronopol, sodium dehydroacetate, polyhexamethylenebiguanide hydrochloride, isothiazolone or diazolidinylurea; sequestering agents such as EDTA salts; perfumes and colourings.

The discolouration of the compositions according to the invention following exposure to light may be measured, for example, as follows.

400 ml of each composition was prepared and filled into two clear, flat-sided, $O_2$-impermeable bottles, for example glass or PET bottles. The filled bottles were stored in the dark until commencement of each experiment. One bottle of each composition was then kept in the dark whilst the other was exposed to natural daylight from a west-facing window. Visual inspection of the bottles over a period of 10 days indicated that the colour intensity increased with the concentration of titanium dioxide and decreased with the concentration of phosphate salt. However, in each of the formulations of Examples 1 to 22 onset of discolouration (i.e. the time at which visible inspection first indicated that discolouration had occurred) was delayed compared with the relevant comparative formulation containing no phosphate salt. In addition, as the level of phosphate salt was increased the onset of discolouration was increasingly retarded. Readings of colour intensity were taken once all the samples had discoloured (96 hours) by measuring the surface reflectance at a minimum of ten different points on the surface of each bottle with a Minolta chromometer and recording mean L-values. The results are shown in Table A.

TABLE A

| | | Examples 1–11 and Comparative Examples A–D (Uncoated $TiO_2$) | | | Examples 12–22 and Comparative Examples E–H (Stearate-coated $TiO_2$) | | |
| --- | --- | --- | --- | --- | --- | --- | --- |
| $TiO_2$ (% w/w) | Phosphate salt (% w/w) | Example | Onset time (hours) | Mean L value (96 hrs) | Example | Onset time (hours) | Mean L value (96 hrs) |
| 1.5 | 0 | C | <1 | 70.4 | G | 4 | 74.5 |
| 1.5 | 0.25 | 7 | 6–28 | 77.4 | 18 | 28 | 80.3 |
| 1.5 | 0.5 | 8 | 28 | 81.6 | 19 | 28–96 | 81.3 |
| 1.5 | 0.75 | 9 | 28–96 | 83.9 | 20 | 96–240 | 82.6 |
| 2.5 | 0 | B | <1 | 67.6 | F | 4 | 75.5 |
| 2.5 | 0.25 | 4 | 4 | 74.8 | 15 | 28 | 80.1 |
| 2.5 | 0.5 | 5 | 6–28 | 78.7 | 16 | 28–96 | 84.0 |
| 2.5 | 0.75 | 6 | 28 | 82.4 | 17 | 28–96 | 82.9 |
| 5 | 0 | A | <1 | 61.9 | E | 4 | 75.7 |
| 5 | 0.25 | 1 | 2 | 66.5 | 12 | 28 | 81.2 |
| 5 | 0.5 | 2 | 4 | 73.5 | 13 | 28 | 81.0 |
| 5 | 0.75 | 3 | 6–28 | 76.8 | 14 | 28–96 | 83.5 |
| 10 | 0 | D | <1 | 56.8 | H | 4 | 73.2 |
| 10 | 0.5 | 10 | 2 | 68.5 | 21 | 28 | 81.2 |
| 10 | 0.75 | 11 | 4 | 72.2 | 22 | 28 | 81.5 |

It was noted that the formulations of Examples 1 to 11 were more rapidly discoloured than those of Examples 12–22. This was due to the use of aluminium stearate-coated titanium dioxide in Examples 12–22 which provides some protection against discolouration.

The surface reflectance of each of the bottles containing emulsions. Comparative Examples A to L form no part of the present invention.

TABLE C

| Formulation Type | Example | Phosphate (%) | pH | L-value (Mean) | | Discolouration (%) |
|---|---|---|---|---|---|---|
| Oil-in-water emulsion 1 | Comparative J | None | 5.4 | Dark | 86.1 | 0 |
| | | | | Light | 54.5 | 100 |
| | 26 | Phosphate (0.5%) | 5.9 | | 59.3 | 85 |
| | 27 | Phosphate (2%) | 5.9 | | 69.4 | 53 |
| | 28 | Phosphate (2%) | 7.4 | | 59.9 | 83 |
| | 29 | Pyrophosphate (2%) | 8.3 | | 58.1 | 88 |
| | 30 | Phosphate (2%) | 11.2 | | 57.4 | 91 |
| | 31 | Phosphoric acid | 3.1 | | 62.1 | 76 |
| | 32 | Phosphate (10%) | 5.6 | | 70.4 | 50 |
| | 37 | Phosphate-coated $TiO_2$ | 7.0 | | 67.1 | 60 |
| Oil-in-water emulsion 2 | Comparative K | None | 7.2 | Dark | 86.5 | 0 |
| | | | | Light | 62.0 | 100 |
| | 33 | Polyphosphate (3%) | 8.4 | | 70.7 | 65 |
| | 34 | Phosphate (3%) | 5.9 | | 77.5 | 37 |
| Water-in-oil emulsion | Comparative L | None | * | Dark | 85.0 | 0 |
| | | | | Light | 68.7 | 100 |
| | 35 | Phosphate (2%) | * | | 70.2 | 91 |
| | 38 | Phosphate-coated $TiO_2$ | * | | 83.9 | 6 |

*Not applicable the parabens formulations of Examples 23 to 25 and comparative Example I was measured using a Minolta chromometer. The mean b-value (yellow discolouration) was recorded after 15 minutes and 15 hours storage. The results are shown in Table B below.

TABLE B

| Formulation | Phosphate salt (% w/w) | b-value (15 mins) | b-value (15 hours) |
|---|---|---|---|
| Comparative Example 1 | 0 | 8.4 | 9.3 |
| Example 23 | 0.25 | 7.1 | 4.1 |
| Example 24 | 0.5 | 5.8 | 2.8 |
| Example 25 | 0.75 | 4.9 | 2.5 |

The results obtained clearly show that increasing levels of phosphate salt in the formulations according to the invention increasingly reduces the amount of yellowing of parabens—containing compositions and even causes a further reduction of yellowness with time.

For rapid determinations of discolouration the compositions according to the invention were filled into 400 ml clear, flat-sided, $O_2$-impermeable bottles. The filled bottles were exposed in a darkened room to UV-A-irradiation using a Uva Hand 250 Black light (Dr Honle GmbH) at a height of approximately 20 cm above the bottle surface for one hour. The Minolta chromometer L-values were recorded and compared with two control samples of a formulation which contained no phosphate, one of which had been similarly exposed to UV-A-irradiation and one of which had been kept in a dark cupboard. A value for the percentage discolouration was calculated from the difference between the sample reading and the readings obtained from the two controls. A minimum of ten chromometer readings were taken at different points on the surface of each bottle. The mean results are given in Table C.

The invention is illustrated by the following Examples 1 to 43, which are given by way of example only. Examples 1 to 34 and 39 to 43 were formulated as oil-in-water emulsions and Examples 35, 38 and 40 are water-in-oil

EXAMPLE 1

| | % w/w |
|---|---|
| 1) Acrylic acid polymer (sold under the trade name Carbopol 934) | 0.1 |
| 2) Hydroxyethylcellulose (sold under the trade name Natrosol 250 HHR) | 0.1 |
| 3) EDTA sodium salt (sold under the trade name Sequestrene Na4) | 0.1 |
| 4) Glycerin | 2.0 |
| 5) 1,3-Butylene glycol | 12.0 |
| 6) Non-ionic self-emulsifying wax (sold under the trade name Polawax) | 1.8 |
| 7) Glyceryl monostearate (sold under the trade name Monostearin NSE Edible Bibby) | 1.8 |
| 8) Trilaurin (sold under the trade name Softisan 100) | 1.0 |
| 9) Capric/caprylic triglyceride (sold under the trade name Migliol 810) | 1.5 |
| 10) White soft paraffin (sold under the trade name MO80 AB & L) | 4.0 |
| 11) Silicone fluid (sold under the trade designation F111/100) | 0.4 |
| 12) Polyvinylpyrrolidone copolymer (sold under the trade name Antaron V216) | 0.5 |
| 13) Light liquid paraffin (sold under the trade designation WOM 14) | 3.0 |
| 14) Potassium hydroxide | 0.027 |
| 15) Titanium dioxide (sold under the trade designation MT150 W) | 5.0 |
| 16) Phosphate salt [Monosodium phosphate:Disodium phosphate (4:1)] | 0.25 |
| 17) Water | ad. 100 |

Components 1 to 5 were dispersed in water and heated to 70° C. Components 6 to 13 were mixed together and heated to 70° C. Component 15 (titanium dioxide) was dispersed into the oil phase (components 6 to 13), mixed with components 1 to 5 and homogenised at 70° C. using a high shear mixer/homogeniser (Silverson). Component 14 (dissolved in a minimal amount of water) and component 16 (dissolved in a minimal amount of water) were added and the mixture cooled to give a lotion. Alternatively, if desired, component 15 (titanium dioxide) may be added into the water phase or after all other components have been formulated.

EXAMPLES 2–11 AND COMPARATIVE EXAMPLES A–D

Different proportions of titanium dioxide and phosphate salt were formulated as described in Example 1 to give lotions. The proportions were as shown in Table 1 (Example 1 included for comparison).

TABLE 1

| Formulation | $TiO_2$ (% w/w) | Phosphate salt (% w/w) |
|---|---|---|
| Example | | |
| 1 | 5.0 | 0.25 |
| 2 | 5.0 | 0.50 |
| 3 | 5.0 | 0.75 |
| 4 | 2.5 | 0.25 |
| 5 | 2.5 | 0.50 |
| 6 | 2.5 | 0.75 |
| 7 | 1.5 | 0.25 |
| 8 | 1.5 | 0.50 |
| 9 | 1.5 | 0.75 |
| 10 | 10.0 | 0.50 |
| 11 | 10.0 | 0.75 |
| Comparative Example | | |
| A | 5.0 | 0 |
| B | 2.5 | 0 |
| C | 1.5 | 0 |
| D | 10.0 | 0 |

EXAMPLE 12

| | % w/w |
|---|---|
| 1) Ethoxylated fatty acid (sold under the trade name Tefose 1500) | 10.0 |
| 2) Isopropyl palmitate | 7.5 |
| 3) Light liquid paraffin (sold under the trade designation WOM14) | 2.0 |
| 4) Ethoxylated triglyceride (sold under the trade name Labrafil M 2130 CS) | 3.0 |
| 5) Stearic acid | 1.0 |
| 6) Titanium dioxide (stearate-coated - sold under the trade designation MT100T) | 5.0 |
| 7) Glycerin | 10.0 |
| 8) Phosphate salt [Monosodium phosphate:disodium phosphate (4:1)] | 0.25 |
| 9) Water | ad. 100 |

Components 1 to 5 were melted together at 70° C. and the titanium dioxide dispersed into the mixture using a high shear mixer/homogeniser (Silverson). Components 7 to 9 were heated to 70° C. and the titanium dioxide mixture added using the Silverson. The resulting mixture was homogenised using a high shear mixer/homogeniser to give a lotion.

EXAMPLES 13–22 AND COMPARATIVE EXAMPLES E–H

Different proportions of titanium dioxide and phosphate salt were formulated as described in Example 12 to give lotions. The proportions were as shown in Table 2 (Example 12 included for comparison).

TABLE 2

| Formulation | $TiO_2$ (% w/w) | Phosphate salt (% w/w) |
|---|---|---|
| Example | | |
| 12 | 5.0 | 0.25 |
| 13 | 5.0 | 0.50 |
| 14 | 5.0 | 0.75 |
| 15 | 2.5 | 0.25 |
| 16 | 2.5 | 0.50 |
| 17 | 2.5 | 0.75 |
| 18 | 1.5 | 0.25 |
| 19 | 1.5 | 0.50 |
| 20 | 1.5 | 0.75 |
| 21 | 10.0 | 0.50 |
| 22 | 10.0 | 0.75 |
| Comparative Example | | |
| E | 5.0 | 0 |
| F | 2.5 | 0 |
| G | 1.5 | 0 |
| H | 10.0 | 0 |

EXAMPLE 23–25 AND COMPARATIVE EXAMPLE I 0.45% Parabens [methyl parabens:propyl parabens (2:1)] was dissolved in components 1 to 5 of each of the formulations of Examples 1 to 3 and Comparative Example A and then formulated as described therein to give lotions. The proportions of parabens and phosphate salt were as shown in Table 3.

TABLE 3

| Formulation | Phosphate salt (% w/w) | Parabens (% w/w) |
|---|---|---|
| Example | | |
| 23 | 0.25 | 0.45 |
| 24 | 0.5 | 0.45 |
| 25 | 0.75 | 0.45 |
| Comparative Example | | |
| I | 0 | 0.45 |

EXAMPLES 26–32 AND COMPARATIVE EXAMPLE J

The titanium dioxide (MT100T) (component 6) and the phosphate salt (component 8) of Example 12 were replaced by 5% titanium dioxide (sold under the trade designation MT150W) and different concentrations and types of phosphates to give the lotion formulations of Examples 26 to 32. Phosphates used were as shown in Table 4.

TABLE 4

| Formulation | Phosphate (concentration) | pH |
|---|---|---|
| Example | | |
| 26 | Monosodium phosphate (0.35%) + Disodium phosphate (0.15%) | 5.9 |
| 27 | Monosodium phosphate (1.4%) + Disodium phosphate (0.6%) | 5.9 |
| 28 | Disodium phosphate (2%) | 7.4 |
| 29 | Tetrasodium pyrophosphate (2%) | 8.3 |
| 30 | Trisodium phosphate (2%) | 11.2 |
| 31 | Phosphoric acid (0.1 ml concd) | 3.1 |
| 32 | Monosodium phosphate (7%) + Disodium phosphate (3%) | 5.6 |
| Comparative Example | | |
| J | None | 5.4 |

EXAMPLE 33

| | % w/w |
|---|---|
| 1) Glycerin | 2.0 |
| 2) Xanthan Gum (sold under the trade name Keltrol) | 0.3 |
| 3) Hydroxymethylcellulose (sold under the trade name Natrosol 250 HHR) | 0.1 |
| 4) Titanium dioxide (sold under the trade designation MT150W) | 3.0 |
| 5) D-Panthenol | 0.67 |
| 6) 1,3-Butylene glycol | 12.0 |
| 7) Stearyl polyoxyethylene alcohol (sold under the trade name Brij 721) | 2.0 |
| 8) Vitamin A palmitate | 0.02 |
| 9) Arachidyl propionate (sold under the trade name Waxenol 801) | 1.0 |
| 10) Evening primrose oil | 1.0 |
| 11) Stearyl polyoxyethylene alcohol (sold under the trade name Brij 72) | 1.0 |
| 12) Glyceryl monostearate (sold under the trade name Monostearin NSE Edible Bibby) | 1.2 |
| 13) Capric/caprylic triglyceride (sold under the trade name Migliol 810) | 1.1 |
| 14) Trilaurin (sold under the trade name Softisan 100) | 0.6 |
| 15) White soft paraffin | 2.5 |
| 16) Light liquid paraffin (sold under the trade designation WOM14) | 1.5 |
| 17) Silicone fluid (sold under the trade designation F111/100) | 1.0 |
| 18) Polyvinylpyrrolidone copolymer (sold under the trade name Antaron V216) | 0.5 |
| 19) Sodium polyphosphate | 3.0 |
| 20) Water | ad. 100 |

Components 2, 3 and 19 were added to the water heated to 70°–75° C. and the mixture dispersed using a high shear mixer/homogeniser (Silverson) for 20 minutes. Components 1 and 6 were mixed together, heated to 70° C. and added to the water dispersion. The titanium dioxide (component 4) dispersed therein using the Silverson. Components 5 and 7 to 18 were heated together to 70°–75° C. and this mixture was added to the water dispersion and mixing continued for 5 minutes to give the lotion of Example 33.

EXAMPLE 34 AND COMPARATIVE EXAMPLE K

The formulation of Example 33 was formulated using an alternative phosphate salt or no phosphate salt at all as shown in Table 5 to give the lotions of Example 34 and Comparative Example K.

TABLE 5

| Formulation | Phosphate salt (concn) | pH |
|---|---|---|
| Comparative Example | | |
| K | None | 7.2 |
| Example | | |
| 33 | Sodium polyphosphate (3%) | 8.4 |
| 34 | Monosodium phosphate (2.4%) + disodium phosphate (0.6%) | 5.9 |

EXAMPLE 35 AND COMPARATIVE EXAMPLE L

| | % w/w |
|---|---|
| 1) Mixture of silicone copolyol and cyclomethicone (sold under the trade designation Silicone Fluid 3225C) | 12.0 |
| 2) Cyclomethicone (sold under the trade designation Silicone Fluid 345DC) | 15.0 |
| 3) Cetyl dimethicone (sold under the trade name Abil B9801) | 5.0 |
| 4) Sorbitan sesquioleate (sold under the trade name Arlacel 83) | 3.0 |
| 5) Glycerol sorbitan fatty acid ester (sold under the trade name Arlacel 481) | 0.7 |
| 6) Butylated hydroxytoluene | 0.05 |
| 7) Titanium dioxide (sold under the trade designation MT150W) | 5.0 |
| 8) Sodium citrate | 4.0 |
| 9) Bronopol | 0.02 |
| 10) Sodium dehydroacetate | 0.15 |
| 11) Phosphate salt [Monosodium phosphate: disodium phosphate (4:1)] | 2.0 |
| 12) Water | ad 100 |

Components 5 and 6 were melted and mixed into components 1 to 4, together with component 7, using a high shear mixer/homogeniser (Silverson). Components 8 to 11 were added to the water and the water phase was added slowly to the oil phase with stirring. The resultant mixture was homogenised using the Silverson to give the cream of Example 35. The phosphate salt (component 11) was omitted in the formulation of Comparative Example L.

EXAMPLE 36

Disodium phosphate salt (100 g) was dissolved in water (200 ml) and 100 g titanium dioxide (sold under the trade designation MT150W) was dispersed therein. The dispersion was allowed to stand for 1 hour and then the titanium dioxide filtered off and washed with water (250 ml). The filtered TiO$_2$ was dried and milled using a pestle and mortar to produce a fine powder. The powder was dispersed into water (200 ml) and then filtered off, dried and ground to give a fine, free-flowing powder of phosphate-coated titanium dioxide particles.

EXAMPLE 37

The phosphate-coated titanium dioxide particles produced according to Example 36 were used to replace the $TiO_2$ and phosphate (components 6 and 8) of the formulation of Example 12 to give the lotion of Example 37.

EXAMPLE 38

The phosphate-coated titanium dioxide particles produced according to Example 36 were used to replace the $TiO_2$ and phosphate (components 7 and 11) of the formulation of Example 35 to give the cream of Example 38.

EXAMPLE 39

Sodium polyphosphate (30 g) was dissolved in water (100 ml) and 30 g titanium dioxide (sold under the trade designation MT150W) was dispersed therein. The dispersion was allowed to stand for 1 hour and then the titanium dioxide filtered off and washed with water (100 ml). The filtered $TiO_2$ was dried and milled using a pestle and mortar to produce a fine powder. The powder was dispersed into water (100 ml) and then filtered off, dried and ground to give a fine, free-flowing powder of polyphosphate-coated titanium dioxide particles.

EXAMPLE 40

The polyphosphate-coated titanium dioxide particles produced according to Example 39 were used to replace the $TiO_2$ and phosphate (components 7 and 11) of the formulation of Example 35 to give the cream of Example 40.

Mean L-value before UV irradiation=83.9

Mean L-value after UV irradiation=85.0

EXAMPLE 43

|   |   | % w/w |
|---|---|---|
| 1) | Ethoxylated fatty acid (sold under the trade name Tefose 1500) | 10.0 |
| 2) | Sunflower oil | 7.5 |
| 3) | Liquid paraffin | 2.0 |
| 4) | Ethoxylated triglyceride (sold under the trade name Labrafil M2130CS) | 3.0 |
| 5) | Stearic acid | 1.0 |
| 6) | Titanium dioxide (sold under the trade designation MT 150W) | 5.0 |
| 7) | Glycerin | 3.0 |
| 8) | Bronopol | 0.02 |
| 9) | Methyl parabens | 0.2 |
| 10) | Propyl parabens | 0.1 |
| 11) | Phosphate salt [monosodium phosphate: disodium phosphate (4:1)] | 2.5 |
| 12) | Water | ad. 100 |

Components 1 to 5 were melted together at 70° C. and titanium dioxide (component 6) dispersed into the mixture using a high shear mixer/homogeniser (Silverson). Components 7 and 12 were heated to 70° C. and components 9 and 10 added with stirring. The two mixtures were then combined. Component 11 (dissolved in a minimal amount of water) was then added and the mixture cooled. Component 8 (dissolved in a minimal amount of water) was added and the mixture homogenised using a high shear mixer/homogeniser to give a lotion. Alternatively, if desired, component 6 (titanium dioxide) may be added into the water phase or after all other components have been formulated.

EXAMPLE 42

The phosphate salt (component 16) of the formulation described in Example 1 was replaced by monosodium phosphate (1.5%) and disodium phosphate (0.5%). 0.4% Parabens blend (sold under the trade name Nipastat) was mixed with components 1 to 5 and then the composition was formulated as described in Example 1 to give a lotion.

EXAMPLE 43

|   |   | % w/w |
|---|---|---|
| 1) | Hydroxyethylcellulose (sold under the trade name Natrosol 250 HHR) | 0.3 |
| 2) | Emulsifier (sold under the trade name Dehydag E) | 1.0 |
| 3) | EDTA sodium salt (sold under the trade name Sequestrene Na4) | 0.1 |
| 4) | Citric acid monohydrate | 0.05 |
| 5) | Isopropyl myristate | 1.5 |
| 6) | Blend of waxes (sold under the trade name Cutina CBS) | 2.0 |
| 7) | Cetostearyl alcohol | 1.0 |
| 8) | Octyl ester of para-aminobenzoic acid | 5.0 |
| 9) | Butylated hydroxytoluene | 0.02 |
| 10) | Titanium dioxide (sold under the trade designation MT 150W) | 3.0 |
| 11) | Phosphate salt [monosodium phosphate: disodium phosphate (4:1)] | 1.5 |
| 12) | Water | ad. 100 |

Components 1 to 4 were dissolved in water at 70° C. Components 5 to 9 were melted together at 70° C. and titanium dioxide (component 10) dispersed into the mixture using a high shear mixer/homogeniser (Silverson). The two mixtures were then combined, component 11 (dissolved in a minimal amount of water) was added and the mixture homogenised to give a lotion. Alternatively, if desired, component 10 (titanium dioxide) may be added into the water phase or after all other components have been formulated.

We claim:

1. A sunscreen composition comprising:
   a) 0.5 to 30% by weight of titanium dioxide having a mean primary particle size of less than 100 nm; and
   b) 0.025 to 30% by weight of phosphate anions wherein the phosphate anions are provided in the form of phosphate salts.

2. A sunscreen composition as claimed in claim 1 wherein the amount of phosphate anions is 0.5 to 300% by weight of the titanium dioxide.

3. A sunscreen composition as claimed in claim 1 wherein the phosphate salt comprises 5 to 150% by weight of the titanium dioxide.

4. A sunscreen composition as claimed in claim 1 wherein the phosphate salt is an alkali metal phosphate.

5. A sunscreen composition as claimed in claim 1 which further comprises 0.01 to 5% by weight of parabens ester.

6. A sunscreen composition as claimed in claim 1 which further comprises 0.1 to 10% by weight of a para-aminobenzoic acid, an ester thereof or a derivative thereof.

7. A sunscreen composition as claimed claim 1 comprising an oil-in-water emulsion which comprises:
   a) 0.5 to 30% by weight of titanium dioxide having a mean primary particle size of less than 100 nm;
   b) 0.025 to 30% by weight of phosphate salt;
   c) 5 to 40% by weight of an oil phase;

d) 1 to 20% by weight of an emulsifier; and e) at least 40% by weight of an aqueous phase.

8. A sunscreen composition as claimed in claim 1 comprising a water-in-oil emulsion which comprises:

a) 0.5 to 30% by weight of titanium dioxide having a mean primary particle size of less than 100 nm;

b) 0.025 to 30% by weight of phosphate salt;

c) 5 to 50% by weight of an oil phase;

d) 1 to 15% by weight of an emulsifier; and e) at least 40% by weight of an aqueous phase.

9. A method of substantially preventing or reducing discoloration of a sunscreen composition containing titanium dioxide which comprises adding phosphate salt in an effective amount which provides a discolouration reducing amount of 0.025–30 weight percent of phosphate anions to said composition.

10. A method according to claim 9 wherein the amount of phosphate anions is 0.5 to 300% by weight of the titanium dioxide.

11. The method of claim 10 wherein the amount of phosphate salt is 3 to 200% by weight of the titanium dioxide.

12. The method of claim 11 in which the phosphate anions constitute 0.025 to 30% by weight of the sunscreen composition.

* * * * *